United States Patent

Hiyama et al.

Patent Number: 4,481,366
Date of Patent: Nov. 6, 1984

[54] PROCESS FOR THE PREPARATION OF A TRIFLUOROVINYLSILANE, AND FLUORINE-CONTAINING POLYMER AND PROCESS FOR ITS PREPARATION

[75] Inventors: Tamejiro Hiyama; Kiyoharu Nishide, both of Sagamihara, Japan

[73] Assignee: Sagami Chemical Research Center, Tokyo, Japan

[21] Appl. No.: 572,247

[22] Filed: Jan. 20, 1984

[30] Foreign Application Priority Data

Jan. 26, 1983 [JP] Japan .................................. 58-9941
Jun. 2, 1983 [JP] Japan .................................. 58-96906

[51] Int. Cl.³ .............................................. C07C 7/08
[52] U.S. Cl. ..................................... 556/431; 556/478; 556/488; 528/14; 528/22; 528/21; 528/23; 526/194; 526/233; 526/236; 526/237
[58] Field of Search ...................... 556/478, 488, 431; 528/14, 22, 21, 23; 526/194, 233, 236, 237

[56] References Cited

U.S. PATENT DOCUMENTS

| | | | |
|---|---|---|---|
| 2,403,370 | 7/1946 | Hurd | 556/478 |
| 2,800,494 | 7/1957 | Haluska | 556/488 X |
| 2,934,515 | 4/1960 | Konkle et al. | 528/14 |
| 3,427,336 | 2/1969 | Van Dyke Tiers | 556/431 |
| 3,818,064 | 6/1974 | Kim | 556/431 |

Primary Examiner—Paul F. Shaver
Attorney, Agent, or Firm—Oblon, Fisher, Spivak, McClelland & Maier

[57] ABSTRACT

A process for preparing a trifluorovinylsilane represented by the general formula:

$$(CF_2=CF)_n SiR_{4-n} \qquad (I)$$

where each R independently represents an alkyl group, an aryl group or an aralkyl group, and n is an integer of 1 to 4, which comprises the reaction of chlorotrifluoroethylene with a chlorosilane represented by the general formula:

$$Cl_n SiR_{4-n} \qquad (II)$$

where R and n are as defined above, in the presence of an alkyllithium. Also disclosed is a fluorine-containing polymer represented by the general formula:

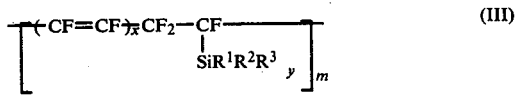

where each of x and m is an integer other than 0, y is an integer including 0, and each of $R^1$, $R^2$ and $R^3$ is a lower alkyl group, an aryl group or an aralkyl group, which is prepared by polymerization of a trifluorovinyl silane (I) with active fluoride-ion generating catalyst.

10 Claims, No Drawings

PROCESS FOR THE PREPARATION OF A TRIFLUOROVINYLSILANE, AND FLUORINE-CONTAINING POLYMER AND PROCESS FOR ITS PREPARATION

The present invention relates to a process for preparing a trifluorovinylsilane, and a novel fluorine-containing polymer and a process for its preparation.

The trifluorovinylsilane is represented by the general formula:

$$(CF_2=CF)_n SiR_{4-n} \qquad (I)$$

where each R independently represents an alkyl group, an aryl group, or an aralkyl group, and n is an integer of 1 to 4.

The trifluorovinylsilane of the formula I prepared by the process of the present invention, is useful as a synthetic reactant to extend a carbon chain by two fluorinated carbon atoms [Inorg. Chem., 1, 78(1962)]. Further, it is useful as a monomer for the preparation of a fluorine-containing polymer.

For the preparation of the trifluorovinylsilane of the formula I, there have been known (a) a method wherein trifluoroethylene is reacted with butyllithium in ether, and then with a chlorosilane [J. Org. Chem., 33, 472(1968)], and (b) a method wherein bromotrifluoroethylene is reacted with magnesium, and then with a chlorosilane [Inorg. Chem., 1, 78(1962)]. However, methods (a) and (b) have drawbacks such that trifluoroethylene and bromotrifluoroethylene used as the starting materials, are extremely expensive, and the yields are low since these methods require two steps.

As a result of an extensive study on the drawbacks of the conventional methods, the present inventors have found it possible to produce the trifluorovinylsilane of the formula I in good yield in a single step from chlorotrifluoroethylene which is readily available at a low cost. The present invention is based on this discovery.

Namely, the present invention provides a process for preparing trifluorovinylsilane represented by the general formula:

$$(CF_2=CF)_n SiR_{4-n} \qquad (I)$$

where each R independently represents an alkyl group, an aryl group or an aralkyl group and n is an integer of 1 to 4, which comprises reacting chlorotrifluoroethylene with a chlorosilane represented by the general formula:

$$Cl_n SiR_{4-n} \qquad (II)$$

where R and n are as defined above, in the presence of an alkyllithium.

The present invention also provides a novel fluorine-containing polymer represented by the general formula:

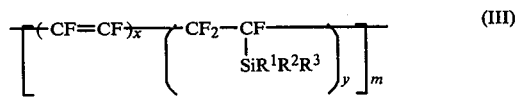

(III)

where each of x and m is an integer other than 0, y is an integer including 0, and each of $R^1$, $R^2$ and $R^3$ is a lower alkyl group, an aryl group or an aralkyl group, and a process for its preparation.

The fluorine-containing polymer of the formula III of the present invention has electric conductivity, and is useful as an electronic material.

Heretofore, polyacetylene has attracted attention as an electrically conductive polymer and has been practically used as an electronic material. (Kagaku Zokan 87, "Synthetic Metal", Published by Kagaku Dozin in 1980). However, polyacetylene has a drawback such that it is unstable in air and susceptible to oxidation. There is a theoretical speculation that this drawback can be overcome by a fluorine substitution of polyacetylene [synthetic metals, 1 321 (1979/80)]. On the other hand, a polydifluoroacetylene is disclosed in Japanese Unexamined Patent Publication No. 59208/1983. However, the polydifluoroacetylene disclosed in this publication is readily soluble in dimethyl sulfoxide or N,N-dimethylformamide, and therefore is considered to be a polymer having a relatively low molecular weight. As a result of extensible studies, the present inventors have found the fluorine-containing polymer of the formula III which is close to the theoretically speculated model and which is insoluble in dimethyl sulfoxide or N,N-dimethylformamide.

The fluorine-containing polymer of the formula III can be prepared by polymerizing a trifluorovinylsilane represented by the general formula:

$$CF_2=CFSiR^1R^2R^3 \qquad (IV)$$

where $R^1$, $R^2$ and $R^3$ are as defined above, in the presence of an active fluoride ion-generating catalyst.

Now, the present invention will be described in detail with reference to the preferred embodiments.

Chlorotrifluoroethylene is used as a starting material in the process for the preparation of the trifluorovinylsilane of the formula I. The starting material is commercially readily available. The chlorosilane of the formula II also is readily available, and it includes, for instance, chlorotrimethylsilane, chlorotriethylsilane, chlorotripropylsilane, chlorotributylsilane, chlorotriphenylsilane, chlorotrivinylsilane, chlorotribenzylsilane, chloromethyldiphenylsilane, chlorodimethyl-t-butylsilane, chlorodimethylisopropylsilane, dichlorodimethylsilane, dichlorodiethylsilane, dichlorodiphenylsilane, dichloromethylphenylsilane, dichlorodivinylsilane, dichloromethyl-t-butylsilane, dichloro-di-t-butylsilane, trichloromethylsilane, trichloroethylsilane, trichlorophenylsilane and tetrachlorosilane.

The reaction of chlorotrifluoroethylene with the chlorosilane of the formula II is conducted in the presence of an alkyllithium. As the alkyllithium, there may be employed butyllithium, s-butyllithium, t-butyllithium or methyllithium. It is preferred to use butyllithium, as it is readily available.

The reaction is preferably conducted in a solvent. As the solvent, there may be employed an ether-type solvent such as tetrahydrofuran, diethyl ether of 1,2-dimethoxyethane, or a hydrocarbon solvent such as pentane, hexane or toluene.

The reaction can be conducted at a temperature of from $-150°$ to $0°$ C. However, it is preferred to conduct the reaction at a temperature of from $-130°$ to $-78°$ C. for good yield.

The trifluorovinylsilane of the formula IV is polymerized in the presence of an active fluoride ion-generating catalyst to obtain the fluorine-containing polymer of the formula III.

The trifluorovinylsilane of the formula IV used as the starting material for the polymerization, can be prepared by reacting commercially readily available chlorotrifluoroethylene or trifluoroethylene with a trialkylchlorosilane in the presence of an alkyllithium, as mentioned above. As the trifluorovinylsilane of the formula IV, there may be mentioned, for instance, trifluorovinyltrimethylsilane, triethyltrifluorovinylsilane, trifluorovinyltripropylsilane, trifluorovinyldimethylphenylsilane, benzyl(trifluorovinyl)dimethylsilane, trifluorovinylmethyldiphenylsilane, bis(trifluorovinyl)diethylsilane, bis(trifluorovinyl)diphenylsilane and tris(trifluorovinyl)phenylsilane.

The polymerization is conducted in the presence of an active fluoride ion-generating catalyst. This catalyst is considered to have not only a function as a polymerization catalyst but also a function to free $FSiR^1R^2R^3$ from the polymer of a monomer of the formula IV to give a polymer of the formula III. For such a catalyst, there may be mentioned an alkali metal fluoride such as potassium fluoride or cesium fluoride; an ammonium fluoride such as tetrabutyl ammonium fluoride, benzyltriethyl ammonium fluoride, trioctyl ammonium fluoride or trimethyl ammonium fluoride; a tris(dialkylamino)sulfonium difluorotrialkylsilicate such as tris(dimethylamino)sulfonium difluorotrimethylsilicate or tris(diethylamino)sulfonium difluorotrimethylsilicate; and a phosphonium fluoride such as tetraoctylphosphonium fluoride. The catalyst is used in a so-called catalytically effective amount.

The polymerization reaction is usually conducted in the absence of a solvent. However, it is possible to use a solvent which does not interfere with the polymerization reaction, such as the dichloromethane, toluene or tetrahydrofuran. The reaction temperature varies depending upon the type of the trifluorovinylsilane or the catalyst used, but is usually within a range of from $-10°$ to $200°$ C. When a trifluorovinylsilane having a low boiling point is used, the polymerization may be conducted under pressure.

The polymer thus obtained is stable in air, and it has a black metallic gloss and electric conductivity of a level substantially equivalent to that of silver bromide.

Now, the present invention will be described in further detail with reference to Examples. However, it should be understood that the present invention is by no means restricted by these specific Examples.

EXAMPLE 1

A reactor flushed with argon was cooled with a liquid nitrogen-pentane cooling medium, and 15.0 g (0.129 mol) of chlorotrifluoroetylene was fed into the reactor. To this reactor, 50 ml of anhydrous tetrahydrofuran (THF), 30 ml of diethyl ether (Et$_2$O) and 30 ml of pentane were introduced to bring the concentration of chlorotrifluoroethylene to 1 mmol/ml. Then, 16.1 g (0.107 mol) of chlorotriethylsilane was introduced. The reactor was cooled to $-130°$ C., and then 88 ml (0.140 mol) of a hexane solution of butyllithium (1.6M) was introduced over a period of one hour. Then, the temperature was gradually raised to room temperature over 7.5 hours. The reaction solution was filtered and dried through a column of Celite placed on anhydrous sodium sulfate. The solvent was removed, and the residue was distilled, whereby 17.8 g of triethyltrifluorovinylsilane was obtained as a colorless transparent oil (yield: 85.1%).

bp: 144° C.

$^1$H-NMR(CDCl$_3$): δ, 0.55-1.13(m. 15H).

$^{19}$F-NMR(CDCl$_3$, 15% CFCl$_3$): (ppm is based on CFCl$_3$); 87.15 ppm(dd, J=70.5 and 26.8 Hz), 117.00 ppm(dd, J=115.7 and 70.5 Hz), 198.9 ppm(dd, J=115.7 and 26.8 Hz).

IR(neat): 1720, 1280, 1125, 1040, 740, 725, 710 cm$^{-1}$.

MS m/z(relative intensity): M+196(10.4), 167(63.7), 105(51.4), 95(87.2), 77(51.8), 67(59.5), 53(83.5), 47(36.8), 29(100.0).

Elementary analysis as C$_8$H$_{15}$F$_3$Si Calculated value: C 48.95, H 7.70. Analytical value: C 48.75, H 7.71.

EXAMPLE 2

A colorless transparent oil, 4.87 g (93.0%) of trifluorovinyltripropylsilane was obtained in the same manner as in Example 1 except that 2.66 g (0.023 mol) of chlorotrifluoroethylene, 4.24 g (0.022 mol) of chlorotripropylsilane, 15.6 ml (0.023 mol) of butyllithium (1.47M hexane solution), 10.0 ml of THF, 6.0 ml of Et$_2$O and 60 ml of pentane were used, and the temperature raising time was 3 hours and 45 minutes.

bp: 82°-83° C./15 mmHg.

$^1$H-NMR(CDCl$_3$): δ 0.63-0.87(m, 6H), 1.02(t, J=7.5 Hz, 9H), 1.22-1.63(m, 6H).

$^{19}$F-NMR(CDCl$_3$, CFCl$_3$): (ppm is based on CFCl$_3$) 86.6 ppm(dd, J=69.9 and 26.1 Hz), 115.9 ppm(dd, J=115.0 and 69.9 Hz), 197.3 ppm(dd, J=115.0 and 26.1 Hz).

IR(neat): 2975, 2940, 2880, 1720, 1460, 1280. 1125, 1070, 1035, 1005, 810, 755, 740, 715, 700 cm$^{-1}$.

MS m/z(relative intensity): 195(M+-43) (17.7), 156(17.1), 111(13.8), 109(10.7), 105(15.4), 91(14.3), 81(66.1), 67(11.9), 65(19.7), 63(28.8), 59(10.1), 47(10.9), 43(17.3), 41(100.0), 39(23.2), 29(12.5), 27(19.0).

Elementary analysis as C$_{11}$H$_{21}$F$_3$Si Calculated value: C 55.43, H 8.88. Analytical value: C 55.51, H 8.95.

EXAMPLE 3

A colorless transparent oil, 9.40 g (88.3%) of (trifluorovinyl)dimethylphenylsilane was obtained in the same manner as in Example 1 except that 5.90 g (0.051 mol) of chlorotrifluoroethylene, 8.40 g (0.049 mol) of chlorodimethylphenylsilane, 35.0 ml (0.052 mol) of butyllithium (1.48M hexane solution), 23.0 ml of THF, 14.0 ml of Et$_2$O and 14.0 ml of pentane were used, and the temperature raising time was 3 hours and 10 minutes.

bp: 82°-83° C./17 mmHg.

$^1$H-NMR(CDCl$_3$): δ 0.47(s, 6H), 7.35-7.48(m, 3H), 7.58-7.72(m, 2H).

$^{19}$F-NMR(CDCl$_3$, CFCl$_3$): (ppm is based on CFCl$_3$) 86.3 ppm(dd, J=65.6 and 24.7 Hz), 114.0 ppm(dd, J=115.7 and 65.6 Hz), 197.3 ppm(dd, J=115.7 and 24.7 Hz).

IR(neat): 3090, 2975, 1725, 1425, 1285, 1255, 1130, 1115, 1040, 840, 815, 790, 730, 705, 695 cm$^{-1}$.

MS m/z(relative intensity): M+216(6.5), 201(12.8), 139(44.7), 135(88.2), 121(24.5), 120(35.1), 115(37.9), 101(81.0), 91(34.4), 81(100.0), 77(49.8), 75(41.0), 51(33.1), 47(37.6).

Elementary analysis as $C_{10}H_{11}F_3Si$ Calculated value: C 55.54; H 5.13. Analytical value: C 55.79, H 5.02.

EXAMPLE 4

$CF_2=CFCl + ClSiMe_2CH_2Ph \rightarrow CF_2=CFSiMe_2CH_2Ph$

A colorless transparent oil, 5.07 g (92.9%) of benzyl(trifluorovinyl)dimethylsilane, was obtained in the same manner as Example 1 except that 2.90 g (0.025 mol) of chlorotrifluoroethylene, 4.38 g (0.024 mol) of benzylchlorodimethylsilane, 17.0 ml (0.025 mol) of butyllithium (1.47M hexane solution), 11.4 ml of THF, 6.8 ml of Et$_2$O and 6.8 ml of pentane were used, and the temperature raising time was 8 hours.

bp: 95°–96° C./20 mmHg.

$^1$H-NMR(CDCl$_3$): δ 80.17(s, 6H), 2.25(s, 2H) 6.93–7.33(m, 5H).

$^{19}$F-NMR(CDCl$_3$, CFCl$_3$): (ppm is based on CFCl$_3$) 86.2 ppm(dd, J=67.0 and 24.7 Hz), 114.8 ppm(dd, J=115.0 and 67.0 Hz), 198.0 ppm(dd, J=115.0 and 24.7 Hz).

IR(neat): 3040, 2980, 1725, 1605, 1500, 1450, 1285, 1255, 1130, 1040, 845, 825, 765, 700 cm$^{-1}$.

MS m/z(relative intensity): M+230(8.3), 134(17.5), 133(28.8), 91(34.9), 81(100.0), 77(49.4), 65(20.4), 47(15.7), 39(73.1).

Elementary analysis as $C_{11}H_{13}F_3Si$ Calculated value: C 57.37, H 5.69. Analytical value: C 57.38, H 5.52.

EXAMPLE 5

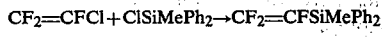

$CF_2=CFCl + ClSiMePh_2 \rightarrow CF_2=CFSiMePh_2$

A colorless transparent oil, 8.94 g (79.3%) of (trifluorovinyl)methyldiphenylsilane, was obtained in the same manner as Example 1 except that 4.80 g (0.041 mol) of chlorotrifluoroethylene, 9.44 g (0.041 mol) of chloromethyldiphenylsilane, 29.0 ml (0.043 mol) of butyllithium (1.48M hexane solution), 18.0 ml of THF, 11.0 ml of Et$_2$O and 11.0 ml of pentane were used, and the temperature raising time was 5 hours and 20 minutes.

bp: 158°–163° C./1.7 mmHg.

$^1$H-NMR(CDCl$_3$): δ 80.73(bs, 3H), 7.25–7.40(m, 6H), 7.40–7.60(m, 4H).

$^{19}$F-NMR(CDCl$_3$, CFCl$_3$): (ppm is based on CFCl$_3$) 84.8 ppm(dd, J=60.7 and 24.7 Hz), 111.8 ppm(dd, J=116.4 and 60.7 Hz), 195.4 ppm(dd, J=116.4 and 24.7 Hz).

IR(neat): 3090, 2970, 1720, 1590, 1490, 1425, 1285, 1275, 1130, 1115, 1040, 795, 730, 695 cm$^{-1}$.

MS m/z(relative intensity): M+278(2.1), 201(24.2), 197(100.0), 178(96.9), 177(22.6), 154(24.5), 152(21.2), 143(37.2), 139(48.1), 120(49.6), 105(22.2), 91(20.8), 81(30.0), 77(95.8), 51(43.6), 47(36.1).

EXAMPLE 6

$2CF_2=CFCl + Cl_2SiEt_2 \rightarrow (CF_2=CF)_2SiEt_2$

A colorless transparent oil, 4.80 g (70.5%) of bis(trifluorovinyl)diethylsilane, was obtained in the same manner as in Example 1 except that 6.75 g (0.058 mol) of chlorotrifluoroethylene, 4.22 g (0.027 mol) of dichlorodiethylsilane, 40.0 ml (0.059 mol) of butyllithium (1.48M hexane solution), 26.4 ml of THF, 15.8 ml of Et$_2$O and 15.8 ml of pentane were used, and the temperature raising time was 8 hours.

bp: 55°–6° C./19 mmHg.

$^1$H-NMR(CDCl$_3$): δ 80.63–2.27(m, 10H). $^{19}$F-NMR(CDCl$_3$, CFCl$_3$): 83.3 ppm(dd, J=60.7 and 25.4 Hz), 112.9 ppm(dd, J=115.0 and 60.7 Hz), 199.9 ppm(dd, J=115.0 and 25.4 Hz).

MS m/e(relative intensity): M+248(2.3), 219(1.8), 195(5.3), 167(3.9), 166(4.0), 141(10.9), 124(8.7), 111(12.1), 109(13.6), 105(47.2), 95(74.3), 87(11.6), 85(33.7), 77(23.7), 67(45.6), 53(25.3), 47(25.3), 29(100.0).

EXAMPLE 7

$2CF_2=CFCl + Cl_2SiPh_2 \rightarrow (CF_2=CF)_2SiPh_2$

Colorless prisms, 9.51 g (88.1%) of bis(trifluorovinyl)diphenylsilane, were obtained in the same manner as Example 1 except that 8.14 g (0.070 mol) of chlorotrifluoroethylene, 7.94 g (0.031 mol) of dichlorophenylsilane, 48.0 ml (0.071 mol) of butyllithium (1.47M hexane solution), 32.0 ml of THF, 19.0 ml of Et$_2$O and 19.0 ml of pentane were used, and the temperature raising time was 5 hours.

mp: 48°–9° C.(hexane).

bp 118°–20° C./0.25 mmHg.

$^1$H-NMR(CDCl$_3$): δ 87.37–7.53(m, 6H), 7.57–7.70(m, 4H).

$^{19}$F-NMR(CDCl$_3$, CFCl$_3$): 80.6 ppm (m of dd, J=52.2 and 24.7 Hz), 107.6 ppm(m of dd, J=120.0 and 52.2 Hz), 196.5 ppm(m of dd, J=120.0 and 24.7 Hz).

IR(KBr): 3075, 1735, 1720, 1595, 1490, 1430, 1305, 1295, 1140, 1120, 1110, 1045, 750, 720, 700, 540, 495 cm$^{-1}$.

MS m/z(relative intensity): M+344(6.5), 267(3.9), 266(3.9), 201(23.7), 182(26.5), 178(26.8), 143(40.7), 120(50.3), 77(100.0), 75(24.8), 51(68.0), 47(26.2).

Elementary analysis as $C_{16}H_{10}F_6Si$ Calculated value: C, 55.81; H, 2.93. Analytical value: C, 55.77; H, 2.91.

EXAMPLE 8

$3CF_2=CFCl + Cl_3SiPh \rightarrow (CF_2=CF)_3SiPh$

A colorless transparent oil, 2.04 g (52.1%) of tris(trifluorovinyl)phenylsilane, was obtained in the same manner as Example 1 except that 3.90 g (0.034 mol) of chlorotrifluoroethylene, 2.39 g (0.0113 mol) of trichlorophenylsilane, 23.8 ml (0.035 mol) of butyllithium (1.47M hexane solution), 15.4 ml of THF, 9.3 ml of Et$_2$O and 9.3 ml of pentane were used, and the temperature raising time was 3 hours.

bp: 97°–8° C./17 mmHg $^1$H-NMR(CDCl$_3$): δ 7.30–7.70(m, 5H).

$^{19}$F-NMR(CDCl$_3$, CFCl$_3$): 78.0 ppm(m of dd, J=45.8 and 24.7 Hz), 107.6 ppm(m of dd, J=118.0 and 45.8 Hz), 200.3 ppm(m of dd, J=118.0 and 24.7 Hz).

MS m/z(relative intensity): M+ 348(4.7), 286(3.4), 267(4.2), 266(4.5), 246(7.1), 217(12.5), 201(23.7), 182(22.4), 158(24.7), 151(48.4), 143(50.2), 120(48.0), 85(34.1), 77(96.0), 75(41.6), 51(100.0), 47(33.8).

EXAMPLE 9

A reactor flushed with argon gas was cooled with a dry ice-ethanol cooling medium, and 2.03 g (0.0174 mol) of chlorotrifluoroethylene was introduced into the reactor. To this reactor, 17 ml of THF was introduced to bring the chlorotrifluoroethylene concentration to 1 mmol/ml, and then 2.35 g (0.016 mol) of chlorotriethylsilane was added. The reactor was cooled to −78° C., and 12 ml (0.018 mol) of butyllithium (1.47M hexane solution) was added in 1 hour. The mixture was stirred at 78° C. for 4 hours and at room temperature for about 1 hour. Workup was conducted in the same manner as in Example 1, whereby 2.64 g (86.2%) of triethyltrifluorovinylsilane was obtained.

EXAMPLE 10

Bis(trifluorovinyl)diethylsilane, 2.78 g (87.5%), was obtained in the same manner as Example 9 except that 3.24 g (0.0278 mol) of chlorotrifluoroethylene, 2.01 g (0.0128 mol) of dichlorodiethylsilane, 19.0 ml (0.028 mol) of butyllithium (1.47M hexane solution) and 27.0 ml of THF, were used, and the mixture was stirred at −78° C. for 3 hours.

EXAMPLE 11

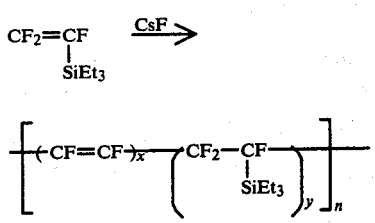

A Schlenk's reactor provided with a condenser was thoroughly dried and flushed with argon gas. Together with 57 mg (0.375 m mol=3.38 mol%) of dried cesium fluoride, 2.18 g (11.10 m mol) of triethyltrifluorosilane was added to the reactor and heated to reflux for 10 days at a bath temperature of 180° C. (whereby a black solid gradually precipitated). The residual liquid was removed by a vacuum pump, and the black solid thereby obtained was dried by heating with a hot gun (a high power drier). The black layer-structured solid was withdrawn under an argon gas stream (214 mg, polymer yield: 31.1%). This solid did not dissolve in water, concentrated sulfuric acid, methanol, ethanol, dichloromethane, o-dichlorobenzene, dimethyl sulfoxide or N,N-dimethylformamide, even when heated to the boiling point. It was soluble in hexamethyl phosphoric triamide at a temperature of from 200° to 230° C. in an amount of 20 mg/ml. The melting point was higher than 300° C. (the weight reduction started at 300° C., and it was almost completely decomposed at 500° C. as measured by a thermobalance).

IR(KBr): 2975, 2900, 2340, 1755(br), 1630(br), 1100(br), 740, 480 cm$^{-1}$.

Average molecular weight (calculated as polystyrene)

1.0-1.2×10$^4$

Elementary analysis: C 36.41; H 2.63%.

As calculated from the values obtained by the elementary analysis, x:y=6:1.

The polymer thus obtained had an electric conductivity σ of 8.5×10$^{-9}$Ω$^{-1}$cm$^{-1}$. When left to stand in air for 6 months, no reduction in the electric conductivity was observed.

EXAMPLE 12

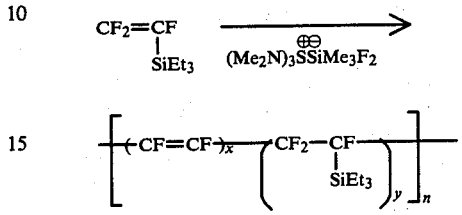

A reactor provided with a condenser was thoroughly dried and flushed with argon gas. Then, 40 mg (0.145 m mol=3.44 mol%) of tris(dimethylamino)sulfonium difluorotrimethylsilicate was introduced, and 827 mg (0.145 m mol) of triethyltrifluorovinylsilane was added at room temperature. The surface of the catalyst turned black. After 20 minutes, the mixture was heated at 100° C. for 3 days. The formed black layer-structured solid was washed with 30 ml of dichloromethane, 30 ml of deaerated water and 30 ml of methanol. Then, the solid was vacuum dried at 100° C. for 12 hours, whereby 70 mg of a black layer-structured solid was obtained. (Polymer yield: 26.8%). This solid was insoluble in water, concentrated sulfuric acid, methanol, ethanol, dichloromethane, o-dichlorobenzene, dimethyl sulfoxide, or N,N-dimethylformamide, even when heated to the boiling point. It was soluble in hexamethyl phosphoric triamide at a temperature of from 200° to 230° C. in an amount of 20 mg/ml.

The melting poing was higher than 300° C. (the weight reduction started at 300° C., and it was almost completely decomposed at 500° C. as measured by a thermobalance).

IR(KBr): 2970, 1740(br), 1640(br), 1180(br), 945, 910, 740 cm$^{-1}$.

Average molecular weight (calculated as polystyrene) 2.1×10$^4$

Elementary analysis: C, 43.53; H, 1.94%. σ=1.67×10$^{-10}$Ω$^{-1}$cm$^{-1}$.

EXAMPLE 13

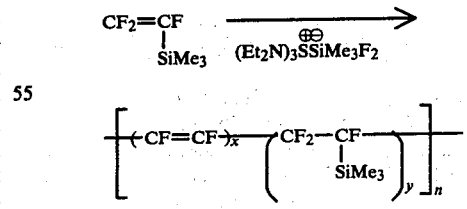

A reactor provided with a condenser, was thoroughly dried and flushed with argon gas. 466 mg (3.02 mmol) of trifluorovinyltrimethylsilane was added, and then 55 mg (0.165 m mol=5.48 mol%) of tris(diethylamino)sulfonium difluorotrimethylsilicate was introduced at room temperature. The polymerization started at room temperature. After 15 minutes, the mixture was heated to reflux at an oil bath temperature of from 80° to 85° C. for 18 hours. The black layer-structured solid thereby obtained was filtered, and washed with 50 ml of dichloromethane, 50 ml of deaerated water and 50 ml of methanol. Then, it was vacuum-dried under heating at 100° C. for 24 hours, whereby 100 mg of a black layer-structured solid was obtained. (Polymer yield: 53.3%). This solid was insoluble in water, concentrated sulfuric acid, methanol, ethanol, dichloromethane, o-dichlorobenzene, dimethyl sulfoxide or N,N-dimethylformamide, even when heated to the boiling point. It was soluble in hexamethyl phosphoric triamide at a temperature of from 200° to 230° C. in an amount of 20 mg/ml. The melting point was higher than 300° C. (the weight reduction started at 300° C., and it was almost completely decomposed at 500° C.).

IR(KBr): 3000, 2230, 1620(br), 1450(br), 1180(br), 740(br) cm$^{-1}$.

The average molecular weight (calculated as polystyrene) was the same as Example 12.

Elementary analysis: C, 42.01; H, 1.73%. $\sigma = 2.38 \times 10^{-10} \Omega^{-1}$ cm$^{-1}$.

We claim:

1. A process for preparing a trifluorovinylsilane represented by the general formula:

$$(CF_2=CF)_n SiR_{4-n} \qquad (I)$$

where each R independently represents an alkyl group, an aryl group or an aralkyl group, and n is an integer of 1 to 4, which comprises reacting chlorotrifluoroethylene with a chlorosilane represented by the general formula:

$$Cl_n SiR_{4-n} \qquad (II)$$

where R and n are as defined above, in the presence of an alkyllithium.

2. A process according to claim 1, wherein the alkyllithium is butyllithium, s-butyllithium, t-butyllithium or methyllithium.

3. The process according to claim 1, wherein the reaction is conducted in a solvent selected from the group consisting of tetrahydrofuran, diethyl ether, 1,2-dimethoxyethane, pentane, hexane or toluene.

4. The process according to claim 1, wherein the reaction is conducted at a temperature of from −150° to 0° C.

5. The process according to claim 1, wherein the chlorosilane is chlorotrimethylsilane, chlorotriethyhlsilane, chlorotripropylsilane, chlorotributylsilane, chlorotriphenylsilane, chlorotrivinylsilane, chlorotribenzylsilane, chloromethyldiphenylsilane, chlorodimethyl-t-butylsilane, chlorodimethylisopropylsilane, dichlorodimethylsilane, dichlorodiethylsilane, dichlorodiphenylsilane, dichloromethylphenylsilane, dichlorodivinylsilane, dichloromethyl-t-butylsilane, dichloro-di-t-butylsilane, trichloromethylsilane, trichloroethylsilane, trichlorophenylsilane or tetrachlorosilane.

6. A fluorine-containing polymer represented by the general formula:

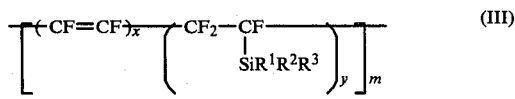

where each of x and m is an integer other than 0, y is an integer including 0, and each of R$^1$, R$^2$ and R$^3$ is a lower alkyl group, an aryl group or an aralkyl group.

7. The fluorine-containing polymer according to claim 6, wherein each of R$^1$, R$^2$ and R$^3$ is a methyl group or an ethyl group.

8. A process for preparing a fluorine-containing polymer represented by the general formula:

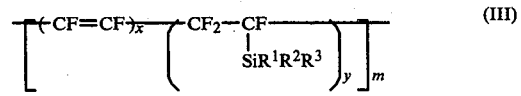

where each of x and m is an integer other than 0, y is an integer including 0, and each of R$^1$, R$^2$ and R$^3$ is a lower alkyl group, an aryl group or an aralkyl group, which comprises polymerizing a trifluorovinylsilane represented by the general formula:

$$CF_2=CFSiR^1R^2R^3 \qquad (IV)$$

where R$^1$, R$^2$ and R$^3$ are as defined above, in the presence of an active fluoride ion-generating catalyst.

9. The process according to claim 8, wherein the active fluoride ion-generating catalyst is an alkali metal fluoride, an ammonium fluoride, a phosphonium fluoride, or a tris(dialkylamino)sulfonium difluorotrialkylsilicate.

10. The process according to claim 8, wherein the polymerization is conducted at a temperature of from −10° to 200° C.

* * * * *